(12) United States Patent
Belelie

(10) Patent No.: US 7,705,065 B2
(45) Date of Patent: Apr. 27, 2010

(54) PHOTOINITIATOR FUNCTIONALIZED WITH ALKOXY GROUPS

(75) Inventor: Jennifer L. Belelie, Oakville (CA)

(73) Assignee: Xerox Corporation, Norwalk, CT (US)

( * ) Notice: Subject to any disclaimer, the term of this patent is extended or adjusted under 35 U.S.C. 154(b) by 338 days.

(21) Appl. No.: 11/846,242

(22) Filed: Aug. 28, 2007

(65) Prior Publication Data

US 2009/0062418 A1    Mar. 5, 2009

(51) Int. Cl.
*C07F 9/00* (2006.01)
*C07C 321/22* (2006.01)
*C07C 49/00* (2006.01)
*C08F 2/50* (2006.01)

(52) U.S. Cl. .................... 522/37; 522/42; 522/53; 522/64; 568/14; 568/42; 568/331; 568/337

(58) Field of Classification Search ............ 522/37, 522/72, 53, 64, 182–183, 42; 560/9, 61, 560/55, 63, 89, 93; 568/335, 336, 337, 13–15, 568/319, 322
See application file for complete search history.

(56) References Cited

U.S. PATENT DOCUMENTS

| | | | |
|---|---|---|---|
| 4,602,097 A * | 7/1986 | Curtis | 549/27 |
| 4,681,950 A * | 7/1987 | Fischer et al. | 549/27 |
| 4,861,916 A * | 8/1989 | Kohler et al. | 568/337 |
| 5,231,135 A | 7/1993 | Machell et al. | |
| 5,532,112 A | 7/1996 | Kohler et al. | |
| 5,621,022 A | 4/1997 | Jaeger et al. | |
| 6,596,786 B2 | 7/2003 | Purvis et al. | |
| 2006/0270754 A1 | 11/2006 | Belelie | |

* cited by examiner

*Primary Examiner*—Susan W Berman
(74) *Attorney, Agent, or Firm*—Oliff & Berridge, PLC

(57) ABSTRACT

A photoinitiator compound is functionalized with alkoxy groups so as to be soluble in alkoxy-containing monomers. The photoinitiator has a formula of $R^1—(OR^2)_n—OC(=O)—R^3$, wherein $R^1—(OR^2)_n—$ represents an alkoxy group and $R^3$ represents a photoinitiator structure. The photoinitiator may be used in a composition for incorporation into inks.

20 Claims, No Drawings

PHOTOINITIATOR FUNCTIONALIZED WITH ALKOXY GROUPS

BACKGROUND

Described herein are photoinitiators that are soluble in various monomers for use in inks or toners, more particularly for use in ultraviolet (UV) curable inks.

For inks, coatings and toners, it is particularly desirable that the photoinitiator be odorless and not affect the color of the ink negatively, for example, by itself exhibiting a color upon curing.

IRGACURE® 2959 is an inexpensive commercially available photoinitiator. However, IRGACURE® 2959 has limited solubility, especially in monomers with alkoxy functional groups such as those used in UV curable inks and coatings. The solubility problem discussed herein leads to incomplete or inconsistent curing which affects image quality and durability. A photoinitiator with improved solubility is desired to address such potential issues.

REFERENCES

Photoinitiators suitable for use in UV curable inks and coatings are known. Further, photoinitiators for the photopolymerization of compounds are known, such as those disclosed in U.S. Pat. No. 5,532,112 (Kohler), which is incorporated in its entirety herein by reference. U.S. Pat. No. 5,532,112 discloses a photoinitiator with a carboxylic acid functional group and the method for making it.

SUMMARY

This disclosure relates to functionalized photoinitiators with solubility in curable monomers, where the photoinitiator is functionalized with one or more alkoxy groups and has a formula of, for example $R^1-(OR^2)_n-Z-C(=O)-R^3$, wherein $R^1-(OR^2)_n-$ represents an alkoxy group, n represents an integer from 1 to 30, Z represents oxygen or a group of the formula $-NR^4-$, wherein $R^4$ is a hydrogen atom, an alkyl group, an aryl group, an arylalkyl group, or an alkylaryl group, and $R^3$ represents a photoinitiator structure.

In embodiments, also described is a method of making a functionalized photoinitiator, the method comprising preparing a photoinitiator and reacting with selected alcohol-ethers to form desired functionalized photoinitiators.

EMBODIMENTS

UV curable ink formulations may comprise a monomer, a photoinitiator and a colorant.

The ink according to one embodiment undergoes a radical curing technique. This means the ink is capable of absorbing radiation and producing free radicals that initiate free radical polymerization of the polymerizable compounds, causing the ink to cure and harden.

The component of the ink that usefully absorbs radiation is the photoinitiator. This absorption of a photon of light promotes an electron from a low energy orbital to a high energy orbital within the photoinitiator molecule. The molecule with an electron in a high energy orbital is in its excited state. From this excited state various pathways can be followed. There are three typical pathways that are useful to effecting cure of the ink. All three pathways ultimately result in the production of a free radical that can react with the carbon-carbon double bond of the acrylate groups found in other ink components.

The three pathways for the excited photoinitiator molecule are: (1) direct fragmentation via homolytic bond cleavage to produce at least one radical of sufficient energy to initiate acrylate polymerization, (2) a bimolecular reaction where the excited molecule abstracts a hydrogen atom from another differently structured molecule and this second molecule initiates acrylate polymerization, and (3) the excited molecule transfers its energy to another differently structured molecule which then initiates polymerization.

Many commercially available photoinitiator compounds are available. Ciba Specialty Chemicals produces a family of photoinitiators for UV curing. One example of a commercially available photoinitiator compound from Ciba is IRGACURE® 2959 [4-(2-hydroxyethyloxy)phenyl-(2-hydroxy-2-propyl) ketone]. IRGACURE® 2959 has many advantages, as it is a low odor, is non-yellowing is relatively inexpensive and is commercially available from Ciba Specialty Chemicals, Inc. IRGACURE® 2959 has a formula:

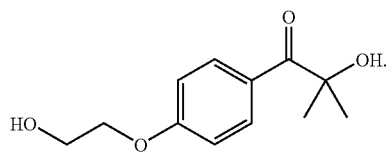

However, this photoinitiator has poor solubility, especially in alkoxy-containing monomers, such as SR9003, that are frequently used in the ink vehicle of UV curable inks. This compound has an ether linkage between the $-CH_2CH_2OH$ group and the benzene ring. However, such is not sufficient to make the photoinitiator compound soluble in alkoxy containing monomers.

The photoinitiators disclosed herein have a formula of $R^1-(OR^2)_n-Z-C(=O)-R^3$, wherein $R^1-(OR^2)_n-$ represents an alkoxy group in which $R^1$ represents an alkyl, arylalkyl, arylalkylene, or alkylarylene as described below, $R^2$ represents an alkylene group as described below, $R^3$ represents a photoinitiator structure, n is an integer from 1 to 30, such as from 1 to 20 or from 1 to 15, and in particular is 2 or 3, representing the number of repeating $(OR^2)$ units and Z represents an oxygen or a group of the formula $-NR^4-$, wherein $R^4$ is a hydrogen atom, an alkyl group, an aryl group, an arylalkyl group, or an alkylaryl group. The inclusion of the alkoxy group renders the photoinitiator compound soluble in alkoxy containing materials used in UV curable ink formulations.

"Alkoxy group" as used herein refers to, for example, any chain exhibiting alkoxy functionality. An alkoxy group is a group in which at least one alkyl group is linked to oxygen, for example $-OCH_3$, $-OCH_2CH_3$, $OCH_2CH_2CH_3$, and the like. The alkoxy chain may be straight, branched and/or substituted.

In embodiments, $R^1-(OR^2)_n-$ is identified as the alkoxy group and may be provided by an alcohol-ether, $R^1-(OR^2)_n-OH$, when Z is O. Suitable examples of $R^1-(OR^2)_n-OH$ include diethylene glycol monomethyl ether to provide the alkoxy group $CH_3(OCH_2CH_2)_2-$, triethylene glycol monomethyl ether to provide the alkoxy group $CH_3(OCH_2CH_2)_3-$, dipropylene glycol monomethyl ether to provide the alkoxy group $CH_3(OC_3H_6)_2-$ and tripropylene glycol monomethyl ether to provide the alkoxy group $CH_3(OC_3H_6)_3-$. All of these alcohol-ethers are commercially available from Sigma-Aldrich Chemical Co. Alternatively, when Z is N, the alkoxy group can be provided by an ether amine. Suitable examples of ether amines include 3-(2-methoxyethoxy)propylamine to provide the alkoxy group $CH_3O(CH_2)_2O(CH_2)_3$—, 3-ethoxy propylamine to provide the alkoxy group $CH_3CH_2O(CH_2)_3$—, 3-methoxy propylamine to provide the alkoxy group $CH_3O(CH_2)_3$— and 3-isopropoxy propylamine to provide the alkoxy group $(CH_3)_2CHO(CH_2)_3$—. All of these ether amines are commercially available from Feixang Chemicals, China. The $R^1$ and $R^2$ groups in $R^1$—$(OR^2)_n$— may be substituted with heteroatoms such as phosphorous, silicon, boron and the like. The $R^1$ and $R^2$ groups may be branched. In embodiments, $R^1$—$(OR^2)_n$— is any alkoxy group having one or more ether linkages therein. Other suitable examples of possible reactants that may provide the alkoxy group include di(ethylene glycol)vinyl ether to provide

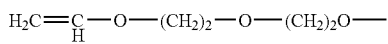

CD570 and CD572, both commercially available from Sartomer Company Inc., Exton, Pa., to provide

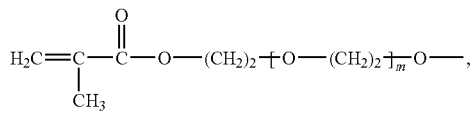

wherein m is an integer representing the number of repeating $[O$—$(CH_2)_2]$ units, and is 2 (from CD570) or 10 (from CD572), and polypropylene glycol monomethacrylate, commercially available from Sartomer Company Inc. as SR604, to provide

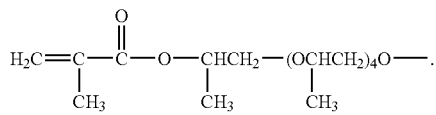

In the examples above, Z from the general formula is the terminal oxygen atom. In embodiments, the alkoxy groups include from 1 to 30 carbon atoms, such as from 10 to 25 carbon atoms or from 10 to 20 carbon atoms. The location of the oxygen atom is not important so long as it is in an ether group, for example.

Z represents oxygen or a group of the formula —$NR^4$—, wherein $R^4$ is a hydrogen atom, an alkyl group, an aryl group, an arylalkyl group, or an alkylaryl group The alkoxy group may impart onto the photoinitiator a high affinity to monomers used in inks. That is, the alkoxy group imparts alkoxy functionality to the photoinitiator such that the photoinitiator compound is soluble in monomers that contain alkoxy moieties, such as frequently used in UV curable inks and coatings. To achieve adequate curing, the photoinitiator is to be uniformly present in the monomer. Conventional photoinitiators that do not contain alkoxy groups may be segregated from the monomer during the formation of the ink. Addition of the alkoxy group avoids this problem by providing the photoinitiator with an affinity for the monomer, and the functionalized photoinitiator is thus adequately soluble in the monomer(s) so as to be substantially uniformly distributed therein.

The photoinitiator moieties, $R^3$, may be any suitable photoinitiator moiety, with the following attributes being desirable: 1) activated by UV radiation, and 2) capable of initiating the curing/polymerization of the curable monomers described herein upon exposure to such UV radiation. The UV sensitivity range may be anywhere in the ultraviolet range, for example, in the range of wavelengths of from about 10 to about 600 nm, such as from about 10 to about 500 nm or from about 10 to about 400 mm.

The photoinitiator moiety includes or is made to include a reactive site, such as a carboxylic acid, hydroxyl or amine group. The compound may be reacted at this reactive site to incorporate the alkoxy group therein in order to functionalize the photoinitiator with an alkoxy group. The reactive site may be, for example, an esterification site, where the photoinitiator may react to chemically bond the carboxylic acid group to the terminal alcohol group of an alcohol-ether.

One suitable general structure of the alkoxy-modified photoinitiator is $R^1$—$(OR^2)_n$—Z—C(=O)—$R^3$ where n is 1 to about 30, such as 1 to about 10; $R^1$ is:

(i) an alkyl group (wherein the alkyl group may be linear or branched, saturated or unsaturated, cyclic or acyclic, and substituted or unsubstituted, and wherein heteroatoms, such as oxygen, nitrogen, sulfur, silicon, phosphorus, boron, and the like either may or may not be present in the alkyl group), in one embodiment with for example 1 to 6 carbon atoms, such as from 1 to 4 or from 1 to 3 carbon atoms, the number of carbon atoms can be outside of these ranges, (ii) an arylalkylene group (wherein the arylalkylene group may be substituted or unsubstituted, wherein the alkyl portion of the arylalkylene group can be linear or branched, saturated or unsaturated, and cyclic or acyclic, and wherein heteroatoms, such as oxygen, nitrogen, sulfur, silicon, phosphorus, boron, and the like either may or may not be present in either the aryl or the alkyl portion of the arylalkylene group), in one embodiment with for example about 6 about 14 carbon atoms, such as from about 6 to about 12 or from about 6 to about 8 carbon atoms, the number of carbon atoms can be outside of these ranges, or (iii) an alkylarylene group (wherein the alkylarylene group may be substituted or unsubstituted alkylarylene groups, wherein the alkyl portion of the alkylarylene group can be linear or branched, saturated or unsaturated, and cyclic or acyclic, and wherein heteroatoms, such as oxygen, nitrogen, sulfur, silicon, phosphorus, boron, and the like either may or may not be present in either the aryl or the alkyl portion of the alkylarylene group), in one embodiment with for example about 6 about 14 carbon atoms, such as from about 6 to about 12 or from about 6 to about 8 carbon atoms. The number of carbon atoms can be outside of these ranges, wherein the substituents on the substituted alkyl, arylalkylene, and alkylarylene groups can be (but are not limited to) halogen atoms, cyano groups, pyridine groups, pyridinium groups, ether groups, aldehyde groups, ketone groups, ester groups, amide groups, carbonyl groups, thiocarbonyl groups, sulfide groups, nitro groups, nitroso groups, acyl groups, azo groups, urethane groups, urea groups, mixtures thereof, and the like, wherein two or more substituents can be joined together to form a ring;

where $R^2$ is:

an alkylene group (wherein an alkylene group is defined as a divalent aliphatic group or alkyl group, including linear and branched, saturated and unsaturated, cyclic and acyclic, and substituted and unsubstituted alkylene groups, and wherein heteroatoms, such as oxygen, nitrogen, sulfur, silicon, phosphorus, boron, and the like either may or may not be present in the alkylene group), in one embodiment with for example about 2 about 6 carbon atoms, such as from about 2 to about 5 or from about 2 to about 4 carbon atoms. The number of carbon atoms can be outside of these ranges, where Z is O or NR⁴ wherein R⁴ is a hydrogen atom, an alkyl group, an aryl group, an arylalkyl group, or an alkylaryl group; and where $R^3$ is a photoinitiating group such as:

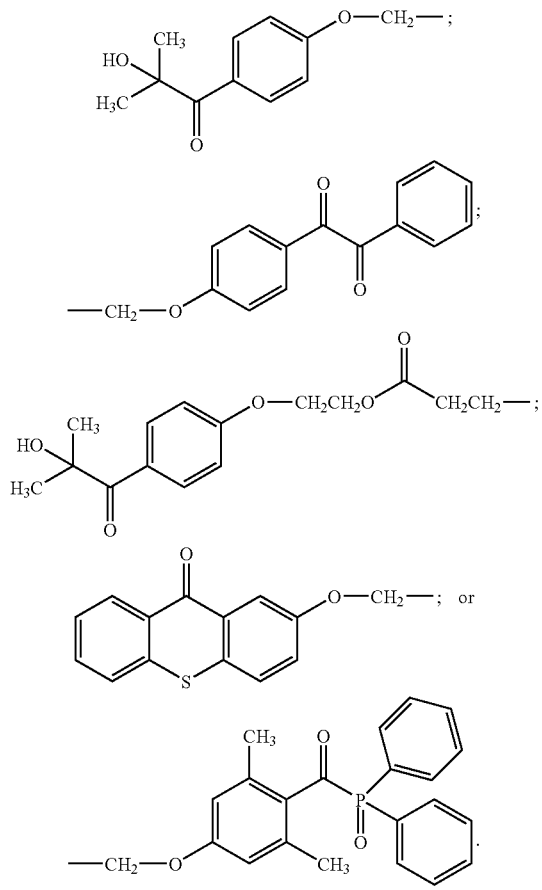

In specific embodiments, $R^1$ is —CH₃, $R^2$ is —CH₂CH₂— or —C₃H₆—, n is 2 or 3, Z is O and $R^3$ is

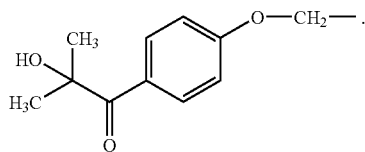

The following discussion illustrates one example of how to functionalize a photoinitiator with an alkoxy group to achieve solubility in UV curable monomers, but other suitable procedures may also be suitably used.

In specific embodiments, the carboxylic acid-modified photoinitiator (6) is formed as illustrated in the reaction scheme below. First, methyl phenoxy acetate (1) undergoes a Friedel-Crafts reaction with isobutyryl chloride (2) and AlCl₃ (3) to produce a ketone ester (4). Second, the ketone ester is brominated to form 5 which is saponified to form carboxylic acid (6).

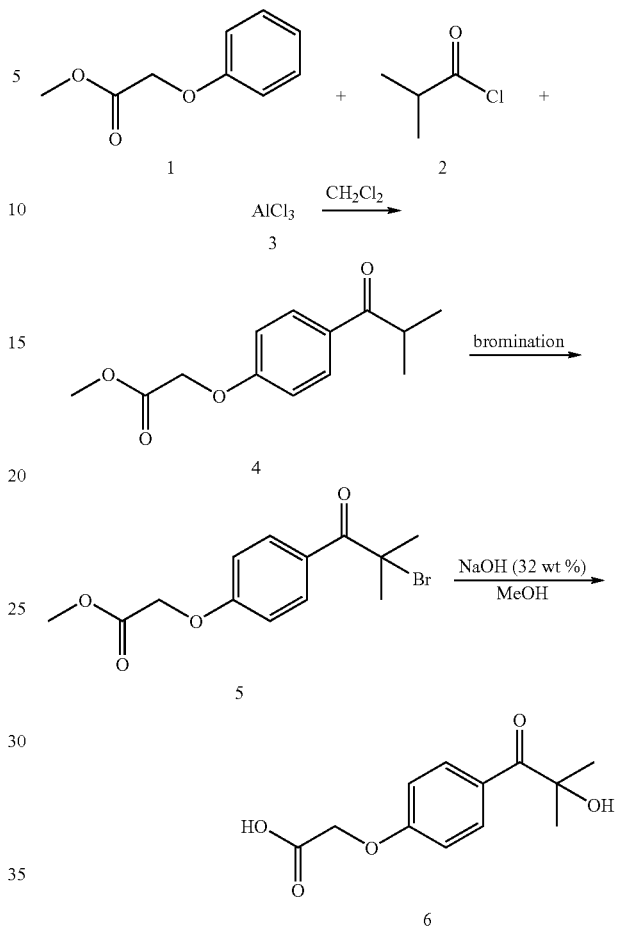

In specific embodiments, the alkoxy-modified photoinitiator is formed as illustrated in the general reaction scheme where carboxylic acid 6 is coupled to alkoxy alcohol 7 to form an ester 8. In the alkoxy alcohol and ester, n is an integer from 1 to 30, for example from 1 to 20, such as from 1 to 15 representing the number of repeating (OR²) units. Examples of suitable coupling agents include 1,3-dicyclohexylcarbodiimide (DCC), of the formula

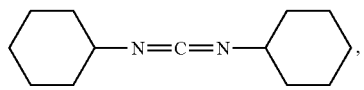

1-[3-(dimethylamino)propyl]3-ethylcarbodiimide HCl (EDCl), N,N-carbonyldiimidazole, N-cyclohexyl-N'-(2-morpholinoethyl)-carbodiimide methyl-p-toluenesulfonate, (benzotriazol-1-yloxy)tris(dimethylamino)phosphonium hexafluorophosphate (BOP), (o-benzotriazol-1-yl)-N,N,N', N'-bis(tetramethylene)uronium hexafluorophosphate (HBTU), bis(2-oxo-3-oxazolidinyl)phosphonic chloride (BOP—Cl), (1H-1,2,3-benzotriazol-1-yloxy)tris(pyrrolidino)phosphonium hexafluorophosphate (PyBOP), and the like, as well as mixtures thereof.

Examples of suitable catalysts for forming the photoinitator include 4-dimethylaminopyridine (DMAP), of the formula

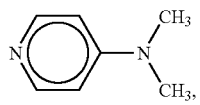

triethylamine, 1,8-diazabicyclo[5.4.0]undec-7-ene (DBU), and the like, as well as mixtures thereof.

Any desired or effective solvent can be employed for forming the photoinitiator. Examples of suitable solvents include methylene chloride, tetrahydrofuran (THF), methyl ethyl ketone, toluene, dimethyl formamide, diethyl ether, hexane, ethyl acetate, and the like, as well as mixtures thereof.

In specific embodiments, 1,3-dicyclohexylcarbodiimide (DCC), catalytic 4-dimethylaminopyridine (DMAP) and THF are used. In the reaction, the alcohol-ether and the compound including the photoinitiator are added such that the alcohol-ether is added in amounts of from 1.0 to 1.1 parts of the photoinitiator compound on a molar equivalent basis.

The UV curable ink includes an alkoxy containing monomer as the ink vehicle. Many commercially available monomers used in UV curable inks and coatings contain alkoxy moieties in their backbones. The general structure of these monomers is R'—O—R" where R' and R" are alkyl groups, linear or branched, with optional substitution.

Possible substituents for the alkyl groups (R' and R") of the monomers include hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring. At least one of R' or R" must contain an acrylate or a methacrylate group.

One such monomer is SR9003 (propoxylated neopentyl glycol diacrylate), commercially available from Sartomer Company, Inc., Exton, Pa.

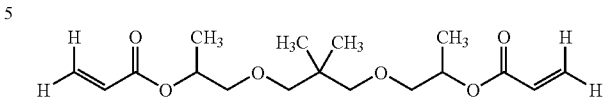

SR9003 has low toxicity and low viscosity. Because of its numerous advantages, it has been used in many applications including UV curable inks and coatings. Other suitable monomers include SR209 (tetraethylene glycol dimethacrylate), SR210 (polyethylene glycol 200 dimethacrylate), SR256 [2-(2-ethoxyethoxy)ethyl acrylate], SR259 (polyethylene glycol (200) diacrylate), SR306 (tripropylene glycol diacrylate esters), SR344 (polyethylene glycol 400 diacrylate), SR348 (ethoxylated (2) bisphenol A dimethacrylate), SR349 (ethoxylated (3) bisphenol A diacrylate), SR355 (ditrimethylolpropane tetraacrylate), SR399 (dipentaerythritol pentacrylate esters), SR399 LV (low viscosity dipentaerythritol pentacrylate esters), SR454 (ethoxylated trimethylolpropane triacrylate esters), SR504 (ethoxylated (4) nonyl phenol acrylate), SR508 (dipropylene glycol diacrylate), SR604 (polypropylene glycol monometharylate), CD9021 (highly propoxylated (5.5) glyceryl triacrylate), SR9020 (propoxylated (3) glycerol triacrylate), and SR9035 (ethoxylated (15) trimethylolpropane triacrylate) all of which are available from Sartomer Company, Inc. The alkoxy group may also be pendant form the chain.

The ink compositions may also contain a colorant, for example a self-dispersible colorant. 'Colorant' refers for example to pigments, dyes, mixtures thereof, such as mixtures of dyes, mixtures of pigments, mixtures of dyes and pigments, and the like. Any desired or effective colorant can be employed in inks, including dyes, pigments, mixtures thereof, and the like, provided that the colorant can be dissolved or dispersed in the ink vehicle. The compositions can be used in combination with conventional ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Ciba-Geigy); Direct Brilliant Pink B (Crompton & Knowles); Aizen Spilon Red C-BH (Hodogaya Chemical); Kayanol Red 3BL (Nippon Kayaku); Levanol Brilliant Red 3BW (Mobay Chemical); Levaderm Lemon Yellow (Mobay Chemical); Spirit Fast Yellow 3G; Aizen Spilon Yellow C-GNH (Hodogaya Chemical); Sirius Supra Yellow GD 167; Cartasol Brilliant Yellow 4GF (Sandoz); Pergasol Yellow CGP (Ciba-Geigy); Orasol Black RLP (Ciba-Geigy); Savinyl Black RLS (Sandoz); Dermacarbon 2GT (Sandoz); Pyrazol Black BG (ICI); Morfast Black Conc. A (Morton-Thiokol); Diaazol Black RN Quad (ICI); Orasol Blue GN (Ciba-Geigy); Savinyl Blue GLS (Sandoz); Luxol Blue MBSN (Morton-Thiokol); Sevron Blue 5GMF (ICI); Basacid Blue 750 (BASF), Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 26050] (BASF), Intratherm Yellow 346 from Crompton and Knowles, C.I. Disperse Yellow 238, Neptune Red Base NB543 (BASF, C.I. Solvent Red 49), Neopen Blue FF-4012 from BASF, Lampronol Black BR from ICI (C.I. Solvent Black 35), Morton Morplas Magenta 36 (C.I. Solvent Red 172), metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. Nos. 5,621,022 and 5,231,135, the disclosures of each of which are totally incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, and uncut Reactant Violet X-80.

Pigments are also suitable colorants for the compositions. Examples of suitable pigments include Violet Toner VT-8015 (Paul Uhlich); Paliogen Violet 5100 (BASF); Paliogen Violet 5890 (BASF); Permanent Violet VT 2645 (Paul Uhlich); Heliogen Green L8730 (BASF); Argyle Green XP-111-S (Paul Uhlich); Brilliant Green Toner GR 0991 (Paul Uhlich); Lithol Scarlet D3700 (BASF); Toluidine Red (Aldrich); Scarlet for Thermoplast NSD PS PA (Ugine Kuhlmann of Canada); E.D. Toluidine Red (Aldrich); Lithol Rubine Toner (Paul Uhlich); Lithol Scarlet 4440 (BASF); Bon Red C (Dominion Color Company); Royal Brilliant Red RD-8192 (Paul Uhlich); Oracet Pink RF (Ciba-Geigy); Paliogen Red 3871 K (BASF); Paliogen Red 3340 (BASF); Lithol Fast Scarlet L4300 (BASF); Heliogen Blue L6900, L7020 (BASF); Heliogen Blue K6902, K6910 (BASF); Heliogen Blue D6840, D7080 (BASF); Sudan Blue OS (BASF); Neopen Blue FF4012 (BASF); PV Fast Blue B2G01 (American Hoechst); Irgalite Blue BCA (Ciba-Geigy); Paliogen Blue 6470 (BASF); Sudan III (Red Orange) (Matheson, Colemen Bell); Sudan II (Orange) (Matheson, Colemen Bell); Sudan Orange G (Aldrich), Sudan Orange 220 (BASF); Paliogen Orange 3040 (BASF); Ortho Orange OR 2673 (Paul Uhlich); Paliogen Yellow 152, 1560 (BASF); Lithol Fast Yellow 0991 K (BASF); Paliotol Yellow 1840 (BASF); Novoperm Yellow FGL (Hoechst); Permanent Yellow YE 0305 (Paul Uhlich); Lumogen Yellow D0790 (BASF); Suco-Yellow L1250 (BASF); Suco-Yellow D1355 (BASF); Suco Fast Yellow D1355, D1351 (BASF); Hostaperm Pink E (American Hoechst); Fanal Pink D4830 (BASF); Cinquasia Magenta (Du Pont); Paliogen Black L0084 (BASF); Pigment Black K801 (BASF); and carbon blacks such as REGAL 330®. (Cabot), Carbon Black 5250, Carbon Black 5750 (Columbia Chemical), IJX-157 (Cabot) and the like.

The colorant is present in any desired or effective amount to obtain the desired color or hue. The colorant may be present in an amount of for example from about 0.1 percent to about 50 percent by weight, such as from about 0.2 percent to about 10 percent by weight, such as from about 0.5 percent to about 3 percent by weight.

Other colors besides the subtractive primary colors can be desirable for applications such as postal marking or industrial marking and labeling, and the invention is applicable to these needs. Further, ultraviolet (UV) absorbing dyes can also be incorporated into the inks for use in applications such as "invisible" coding or marking of products.

In embodiments, a stabilizer may also be included. One suitable example of a stabilizer is IRGASTAB® UV 10, available from Ciba Specialty Chemicals, which increases the long-term stability of inks and coatings. It is a radical scavenger that prevents gelation of UV curable compositions, while having minimal impact on curing speed.

The following examples illustrate preparation of photoinitiators herein.

Example 1

Methyl 2-(4-isobutyrylphenoxy)acetate (4)

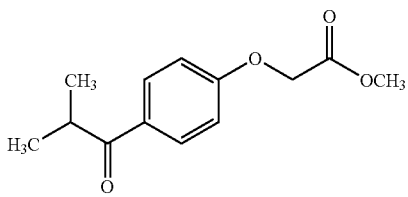

To an oven-dried round bottom flask was added anhydrous $AlCl_3$ (24.1 g, 0.18 mol), which was subsequently purged with Ar. Methylene chloride (10 mL) was added via syringe and the resulting slurry was cooled to 0° C. in an ice bath. The isobutryl chloride (6.9 mL, $6.6 \times 10^{-2}$ mol) was added dropwise via syringe. The methyl phenoxy acetate (8.7 mL, $6.0 \times 10^{-2}$ mol) was added dropwise via syringe. The reaction was stirred until deemed complete by thin layer chromatography (TLC) (25% ethyl acetate in hexane) (approximately 2 h). The reaction mixture was poured slowly into a mixture of ice (100 g) and concentrated HCl (40 mL). The organic layer was separated and the organic layer extracted with methylene chloride (3×100 mL). The combined organic layers were washed with water (3×100 mL) and dried over $MgSO_4$. The solvent was removed in vacuo to reveal 14 g of a white, crystalline solid (quantitative yield). $^1$H NMR (300 NMR, $CDCl_3$) $\delta$7.97 (2H, d, J=8.9 Hz), 6.96 (2H, J=8.9 Hz), 4.71 (2H, s), 3.82 (3H, s), 3.51 (1H, septet, J=6.8 Hz), 1.22 (6H, d, J=6.8 Hz).

4-(Hydroxycarbonylmethoxy)phenyl 2-hydroxy-2-propyl ketone (6)

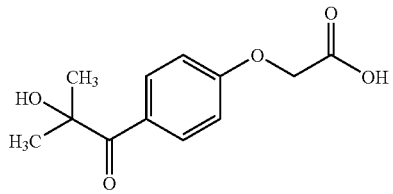

The ketone ester (14 g, $6.0 \times 10^{-2}$ mol) was dissolved in glacial acetic acid (15 mL), followed by the slow, dropwise addition of bromine (3.6 mL, $7.1 \times 10^{-2}$ mol), while stirring. The reaction mixture was stirred at room temperature overnight [deemed complete by TLC (25% ethyl acetate in hexane)]. The reaction mixture was poured into water (150 mL). The product was extracted with ethyl acetate (3×200 mL) and the combined extracts were washed with saturated $NaHCO_3$ (2×200 mL), dried over $MgSO_4$ and concentrated in vacuo. The resulting thick yellow oil was dissolved in methanol (50 mL) and 32% NaOH solution (18 g) was added slowly dropwise while stirring. The reaction mixture was stirred for 10 minutes before the MeOH removed in vacuo. The residue was transferred to water (150 mL), acidified to pH 1 by the dropwise addition of 6M HCl and extracted with ethyl acetate (3×150 mL). The combined organic layers were dried over MgSO$_4$ and concentrated in vacuo. The crude white solid was recrystallized from methylene chloride to afford 6.1 g (43%) of a white crystalline solid. $^1$H NMR (300 NMR, DMSO-d$_6$) δ13.09 (1H, br s), 8.21 (2H, d, J=9.1 Hz), 6.99 (2H, d, J=9.1 Hz), 4.78 (2H, s), 3.32 (1H, br s), 1.39 (6H, s).

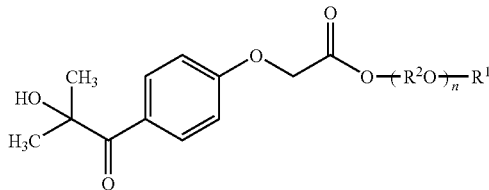

To a round bottom flask equipped with a stopper and septum were added the carboxylic acid (about 1.0 eq.), a desired alcohol-ether (providing the R$^1$—(OR$^2$)$_n$— groups, a-d below) (about 1.1 eq.), N,N-dimethylamino pyridine (DMAP) about (0.1 eq.) and THF (about 1 mL/g carboxylic acid). The reaction mixture was stirred until dissolved. N,N'-Dicyclohexylcarbodiimide (DCC) (about 1.1 eq.) was added portion-wise and the reaction was allowed to run until deemed complete by thin layer chromatography (TLC). The reaction mixture was filtered and the THF was removed from the filtrate in vacuo. The remaining residue was dissolved in ethyl acetate and washed two times with 1M HCl, saturated NaHCO$_3$ and brine. The organic layer was dried over MgSO$_4$, filtered and the solvent removed in vacuo. The residue was purified by column chromatography (EtOAc/hexane).

For photoinitiators 8a-8d below, the following alcohol-ethers were used, respectively: a) diethylene glycol monomethyl ether, b) triethylene glycol monomethyl ether, c) dipropylene glycol monomethyl ether, and d) tripropylene glycol monomethyl ether.

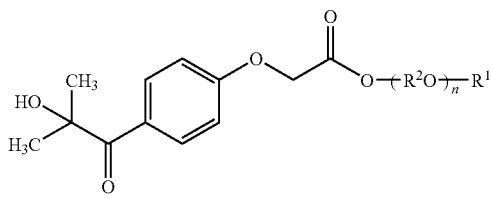

Photoinitiator 8a [R$^1$—(OR$^2$)$_n$—=CH$_3$—(OCH$_2$CH$_2$)$_2$—] was obtained as a colorless oil in about 74% yield. $^1$H NMR (300 NMR, CDCl$_3$) δ8.09 (2H, d, J=9.0 Hz), 6.97 (2H, d, J=9.0 Hz), 4.74 (2H, s), 4.41 (2H, t, J=4.7 Hz), 4.17 (1H, s), 3.75 (2H, t, J=4.7 Hz), 3.64-3.61 (2H, m), 3.56-3.52 (2H, m), 3.39 (3H, s), 1.64-1.60 (6H, m).

Photoinitiator 8b [R$^1$—(OR$^2$)$_n$—=CH$_3$—(OCH$_2$CH$_2$)$_3$—] was obtained as a colorless oil in about 65% yield. $^1$H NMR (300 NMR, CDCl$_3$) δ8.09 (2H, d, J=9.0 Hz), 6.97 (2H, d, J=9.0 Hz), 4.74 (2H, s), 4.40 (2H, t, J=4.7 Hz), 4.18 (1H, s), 3.75 (2H, t, J=4.7 Hz), 3.68-3.58 (6H, m), 3.57-3.53 (2H, m), 3.38 (3H, s), 1.65-1.60 (6H, m).

Photoinitiator 8c [R$^1$—(OR$^2$)$_n$—=CH$_3$—(OC$_3$H$_6$)$_2$—] was obtained as a colorless oil in about 54% yield. $^1$H NMR (300 NMR, CDCl$_3$) δ8.08 (2H, d, J=9.0 Hz), 6.97 (2H, d, J=9.0 Hz), 5.36-5.16 (1H, m), 4.70 (2H, s), 4.28 (1H, br. s), 3.59-3.40 (5H, m), 3.37 (3H, s), 1.60-1.57 (6H, m), 1.29 (3H, d, J=6.7 Hz), 1.15-1.08 (3H, m).

Photoinitiator 8d [R$^1$—(OR$^2$)$_n$—=CH$_3$—(OC$_3$H$_6$)$_3$—] was obtained as a colorless oil in about 52% yield. $^1$H NMR (300 NMR, CDCl$_3$) δ8.08 (2H, d, J=8.3 Hz), 6.97 (2H, d, J=8.3 Hz), 5.30-5.11 (1H, m), 4.70 (2H, s), 4.19 (1H, s), 3.59-3.22 (11H, m), 1.63 (6H, s), 1.28 (3H, d, J=6.1 Hz), 1.16-1.07 (6H, m).

Example 2

The following monomers were used for testing: 1) SR9003 (propoxylated neopentyl glycol diacrylate), 2) SR209 (tetraethylene glycol dimethacrylate), 3) SR399LV (low viscosity dipentaerythritol pentacrylate esters), and 4) SR454 (ethoxylated trimethylolpropane triacrylate esters).

Solutions of about 10 wt % IRGACURE® 2959 were insoluble in the four above-mentioned monomers at room temperature.

Solutions of about 10 wt % of the four photoinitiators (8a, 8b, 8c, and 8d) were prepared in each of the four above monomers (SR9003, SR209, SR399LV and SR454) at about room temperature, approximately 22° C. to 27° C. The above photoinitiators (8a, 8b, 8c, and 8d) were soluble in all four of the above monomers.

The solutions were dropped onto glass slides and exposed to UV light from a LightHammer 6 lamp. SR9003, SR399LV and SR454 formed robust films that could not be scratched at about 230 ft/min. SR209 solutions required 3 passes at about 32 ft/min to produce robust films that could not be scratched. Color changes and odor were not observed upon curing.

Ink Example

SR9003 (about 81.3 g), IRGACURE® 379 (about 2.5 g), 8a (about 3.0 g), IRGACURE® 819 (about 1.0 g) and IRGASTAB® UV10 (about 0.2 g) are heated while stirring for 1 hour. This solution is added slowly dropwise to about a 25 wt % cyan pigment dispersion (about 12.0 g) at about 90° C. while stirring. The complete ink is stirred at about 90° C. for about an additional 1 hour. The ink is filtered to about 6 µm.

The ink is printed at a temperature at which its viscosity is from about 10 to about 12 cps on a PHASER® 860 printer (modified to change the intermediate transfer drum temperature, paper preheating temperature, and ink heating temperature) directly onto paper attached to an intermediate transfer member at about 30° C. and then exposed to UV light at a remote curing station or from an in-line source. The ink is printed on XEROX® 4024, HAMMERMILL® (International Paper), XEROX® Digital Color Gloss and Pasadena Litho Label papers.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims. Unless specifically recited in a claim, step or components of claims should not be implied or imported from the specification or any other claims as to any particular order, number, position, size, shape, angle, color or material.

What is claimed is:

1. An alkoxy functionalized photoinitiator soluble in alkoxy moiety containing monomers, and having a formula R$^1$—(OR$^2$)$_n$—Z—C(=O)—R$^3$, wherein R$^1$—(OR$^2$)$_n$— represents an alkoxy group, Z represents an oxygen atom or a group of the formula —NR$^4$—, R$^3$ represents a photoinitiator structure, and n represents an integer from 1 to 30 and wherein R⁴ is selected from the group consisting a hydrogen atom, an alkyl group, an aryl group, an arylalkyl group, or an alkylaryl group.

2. The photoinitiator according to claim 1, wherein the photoinitiator is activated upon exposure to UV light.

3. The photoinitiator according to claim 2, wherein the UV light is of a wavelength of about 10 nm to about 400 nm.

4. The photoinitiator according to claim 1, wherein the alkoxy group, $R^1$—$(OR^2)_n$—, is a linear or branched, substituted or unsubstituted group with from 1 to about 30 carbon atoms.

5. The photoinitiator according to claim 1, wherein $R^3$ represented by a structure selected from the group consisting of

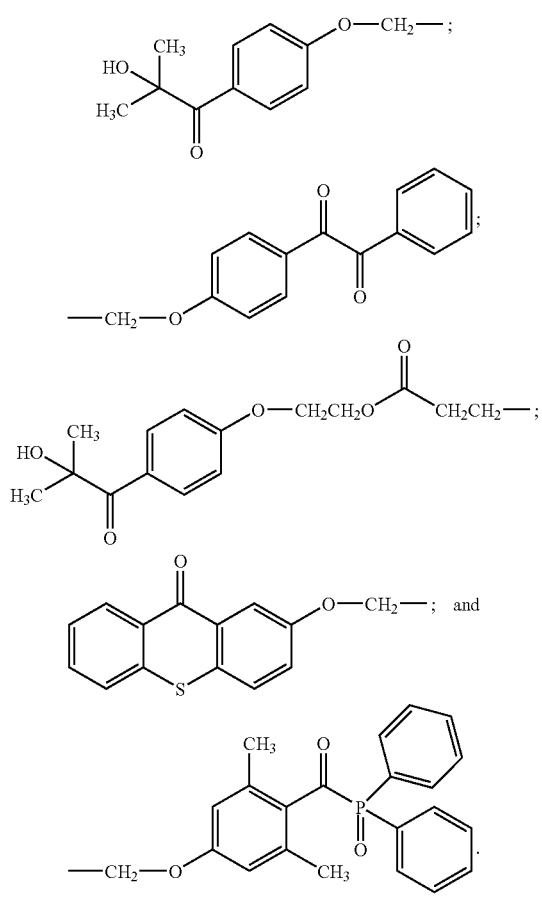

6. The photoinitiator according to claim 1, wherein the alkoxy functionalized photoinitiator has the formula

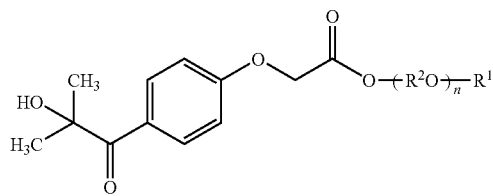

wherein $R^1$ is —$CH_3$, $R^2$ is selected from the group consisting of —$CH_2CH_2$—, and —$C_3H_6$— and n is an integer from 1 to 30.

7. The photoinitiator according to claim 1, wherein $R^1$ is —$CH_3$ and $R^2$ is selected from the group consisting of —$CH_2CH_2$—, and —$C_3H_6$—.

8. The photoinitiator according to claim 1, wherein n is 2 or 3.

9. A method of making a photoinitiator comprising:
reacting the carboxylic acid functionality of a compound HOC(=O)—$R^3$ wherein $R^3$ represents a photoinitiator structure with an alcohol-ether, $R^1$—$(OR^2)_n$—OH, to provide an alkoxy group $R^1$—$(OR^2)_n$— and form an alkoxy functionalized photoinitiator having a formula $R^1$—$(OR^2)_n$—OC(=O)—$R^3$, wherein $R^1$—$(OR^2)_n$— represents an alkoxy group, n represents an integer from 1 to 30, and $R^3$ represents a photoinitiator structure.

10. The method according to claim 9, wherein the alcohol-ether is selected from the group consisting of diethethylene glycol monomethyl ether ($CH_3(OCH_2CH_2)_2OH$), triethylene glycol monomethyl ether ($CH_3(OCH_2CH_2)_3OH$), dipropylene glycol monomethyl ether ($CH_3(OC_3H_6)_2OH$) and tripropylene glycol monomethyl ether ($CH_3(OC_3H_6)_3OH$).

11. A composition comprising an alkoxy moiety containing monomer and an alkoxy functionalized photoinitiator, wherein the photoinitiator is activated by exposure to UV radiation, and wherein the photoinitiator has a formula $R^1$—$(OR^2)_n$—OC(=O)—$R^3$, wherein $R^1$—$(OR^2)_n$— represents an alkoxy group, n represents an integer from 1 to 30, and $R^3$ represents a photoinitiator structure.

12. The composition according to claim 11, wherein the alkoxy group is a linear or branched, substituted or unsubstituted group with from 1 to about 30 carbon atoms.

13. The composition according to claim 11, wherein $R^3$ is represented by a structure selected from the group consisting of

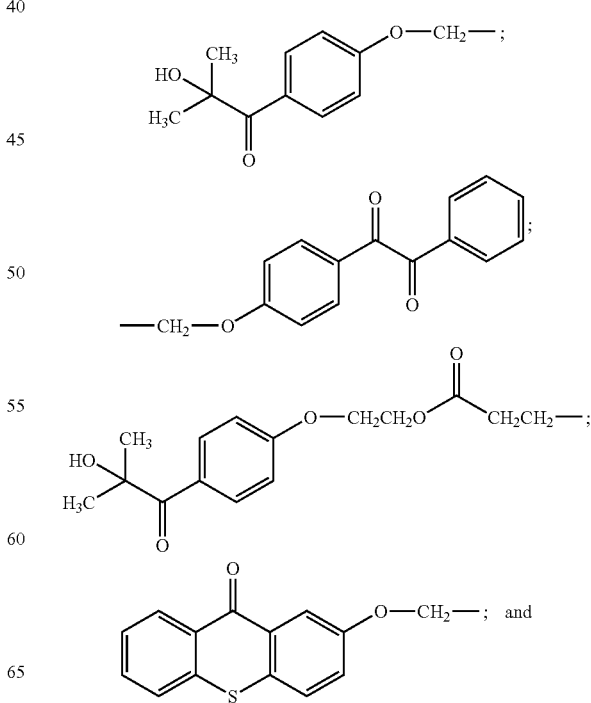

-continued

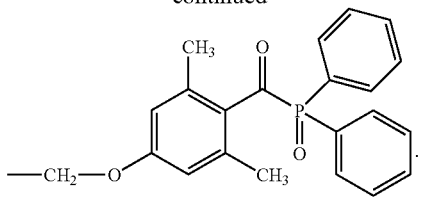

14. The composition according to claim 11, wherein the alkoxy functionalized photoinitiator has a formula

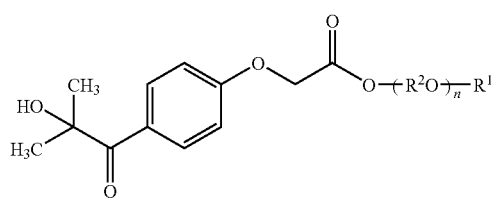

wherein $R^1$ is —$CH_3$ and $R^2$ is selected from —$CH_2CH_2$—, and —$C_3H_6$—.

15. The composition according to claim 11, wherein the monomer is selected from the group consisting of 1) propoxylated neopentyl glycol diacrylate, 2) low viscosity dipentaerythritol pentacrylate esters, 3) ethoxylated trimethylolpropane triacrylate esters, 4) tetraethylene glycol dimethacrylate and mixtures thereof.

16. The composition according to claim 11, wherein $R^1$ is $CH_3$— and $R^2$ is derived from the group consisting of —$CH_2CH_2$— or —$C_3H_6$—.

17. The composition according to claim 11, wherein the monomer comprises from about 85 to about 95 weight percent of the composition.

18. The composition according to claim 11, wherein the photoinitiator comprises from about 5 to about 15 weight percent of the composition.

19. The composition according to claim 11, wherein the composition is cured upon exposure to UV light having a wavelength of from about 10 nm to about 400 nm.

20. The composition according to claim 11, wherein the composition further comprises a colorant.

* * * * *